United States Patent [19]

Sugihara et al.

[11] Patent Number: 4,861,455

[45] Date of Patent: Aug. 29, 1989

[54] ELECTRODE MEMBRANE

[75] Inventors: Hideki Sugihara; Kazuhisa Hiratani; Tatsuhiro Okada, all of Tsukuba, Japan

[73] Assignee: Director General of Agency of Industrial Science and Technology, Tokyo, Japan

[21] Appl. No.: 174,040

[22] Filed: Mar. 28, 1988

[30] Foreign Application Priority Data

Oct. 13, 1987 [JP] Japan .................................. 62-257535

[51] Int. Cl.⁴ ........................................... G01N 27/46
[52] U.S. Cl. ..................................... 204/418; 204/1 T
[58] Field of Search ......................... 204/1 A, 416, 418

[56] References Cited

U.S. PATENT DOCUMENTS 3,856,649 12/1974 Genshaw et al. ................... 204/418
4,770,759 9/1988 Young et al. ....................... 204/418

Primary Examiner—T. Tung
Attorney, Agent, or Firm—Wyatt, Gerber, Burke and Badie

[57] ABSTRACT

The electrode membrane of the invention has high ion-selectivity for lithium ions relative to other alkali and alkaline earth metal ions. The membrane is shaped from a polymeric composition comprising a polymeric material, e.g., a polyvinyl chloride resin and poly(1,2-butadiene), a plasticizer and, as the ion carrier, a derivative of 1,10-phenanthroline such as 2,9-dimethyl-1,10-phenanthroline and 2,9-dimethyl-4,7-diphenyl-1,10-phenanthroline.

9 Claims, 1 Drawing Sheet

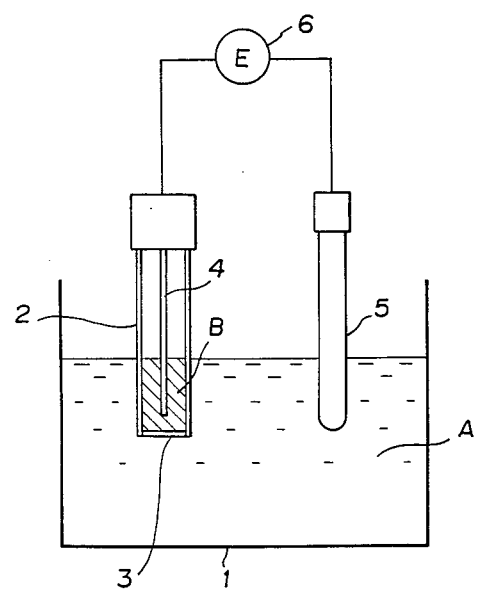

ELECTRODE MEMBRANE

BACKGROUND OF THE INVENTION

The present invention relates to an electrode membrane having selectivity for lithium ions.

It is eagerly desired to develop reliable lithium ion-sensitive electrode membranes used, for example, for the determination of lithium ions in blood serum in the clinical inspection of patients suffering from manic depressive pyschosis.

Various types of polymeric membranes have been hitherto proposed and studies to provide a membrane electrode having selectivity for lithium ions. The polymeric membrane of this kind has a basic structure formed of a polymeric composition composed of a film-forming polymeric resin, a plasticizer, an ion-sensitive substance called an ion carrier and, optionally, an alkali metal salt of a hydrophobic anion. For example, a lithium ion-selective polymeric electrode membrane can be prepared from a polymeric composition comprising a polyvinyl chloride resin, a plasticizer such as 2-nitrophenyl octyl ether, an ion carrier such as N,N'-diheptyl-N,N'-5,5-tetramethyl-3,7-dioxsanonane diamide and, according to need, an alkali metal salt of a hydrophobic anion [see, for example, E. Metzger et al., Helv. Chim. Acta, volume 69, page 1821 (1986) and K. Kimura et al., J. Chem. Soc. Perkin Trans., II, 1986, page 1945].

None of these lithium ion-selective polymeric membranes, however, is quite satisfactory in respect of the selectivity for lithium ions relative to other alkali and alkaline earth metal ions.

SUMMARY OF THE INVENTION

An object of the present invention is therefore to provide a novel polymeric electrode membrane having outstandingly high selectivity for lithium ions not obtained in any prior art membranes.

Thus, the present invention provides an electrode membrane having selectivity for lithium ions which is shaped from a polymeric composition comprising, in admixture:

(a) a polymeric material;
(b) a plasticizer; and
(c) an aromatic compound having a structure of 1,10-phenanthroline represented by the general formula

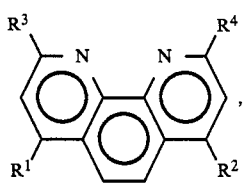

in which $R^1$ and $R^2$ are each an atom or group selected from the class consisting of a hydrogen atom, alkyl groups, aryl groups and aralkyl groups and $R^3$ and $R^4$ are each a group selected from the class consisting of alkyl groups, aryl groups and aralkyl groups.

BRIEF DESCRIPTION OF THE DRAWING

The FIGURE is a schematic illustration of an assembly for the measurement of the activity of cations by using the electrode membrane of the present invention.

DETAILED DESCRIPTION OF THE PREFERRED EMBODIMENTS

The polymeric resin, which is the base ingredient as the component (a) in the polymeric composition from which the inventive electrode membrane is formed, is not particularly limitative and various polymeric materials conventionally used in electrode membranes can be used including synthetic and natural polymeric materials exemplified by polymers and copolymers of ethylenically unsaturated monomers such as polyvinyl chlorides, polyethylenes, poly(1,2-butadienes) and the like, polycondensation polymers such as polyesters, polyamides and the like, polymers by ring-opening polymerization such as epoxy resins and the like, silicone rubbers, urushi resin and so on.

The component (b) in the polymeric composition forming the inventive electrode membrane is a plasticizer which is also not particularly limitative including conventionally used ones such as dialkyl aryl phosphonates, trialkyl phosphates, trialkyl phosphites, dialkyl sebacates, dialkyl adipates, dialkyl phthalates, nitrophenyl alkyl ethers, 2-nitrophenyl aryl ethers and the like. These plasticizers can be used either singly or as a combination of two kinds or more according to need.

The component (c), which is the most characteristic ingredient in the polymeric composition forming the inventive electrode membrane, is a compound represented by the above given general formula (I), in which the symbols $R^1$, $R^2$, $R^3$ and $R^4$ each have the meaning defined above, and serves as an ion carrier. The compound is a derivative of 1,10-phenanthroline including various compounds corresponding to the kinds and combinations of the groups denoted by $R^1$, $R^2$, $R^3$ and $R^4$. Examples of preferable derivatives of 1,10-phenanthroline are 2,9-dimethyl-1,10-phenanthroline, 2,9-dimethyl-4,7-diphenyl-1,10-phenanthroline, 2,9-dibutyl-1,10-phenanthroline, 2,9-dibutyl-4,7-diphenyl-1,10-phenanthroline, 2,9-dioctyl-1,10-phenanthroline, 2,9-dibenzyl-1,10-phenanthroline, 2,9-diphenyl-1,10-phenanthroline and the like though not particularly limited thereto. It is optional that the polymeric composition is further admixed with various known additives including alkali metal salts of a hydrophobic anion such as alkali metal salts of tetraphenyl boric acid, optionally, substituted on the aromatic nuclei with substituents such as halogen atoms.

The compounding proportion of the above described components to form the polymeric composition is such that 100 parts by weight of the polymeric material as the component (a) are compounded with 10 to 300 parts by weight or, preferably, 200 to 260 parts by weight of the plasticizer as the component (b), 0.1 to 15 parts by weight or, preferably, 0.5 to 10 parts by weight of the ion carrier as the component (c) and, when added, 0.5 to 15 parts by weight or, preferably, 3 to 5 parts by weight of the alkali metal salt of a hydrophobic anion.

The above described polymeric composition can be shaped into a membrane by a method of, for example, casting of a solution containing the component ingredients. The membrane should preferably has a thickness in the range from 0.02 to 1.0 mm. The membrane serves as a liquid-film type ion-selective electrode membrane.

Namely, the polymeric membrane is used as a partition membrane and, when it is contacted with a sample solution containing various kinds of ions on one surface and with a reference solution containing the cations of a specific kind in a known concentration on the other surface, a potential difference is produced between the surfaces of the membrane, from which the activity of the cations in the sample solution can be determined.

The procedure for the determination of the activity of cations in a sample solution by use of the inventive electrode membrane is described below with reference to the FIGURE in the accompanying drawing which is a schematic illustration of a typical assembly for the determination of the potential difference between the surfaces of the membrane. The sample solution A in the vessel 1, which is usually an aqueous solution, contains the objective cations in an unknown concentration. A cylindrical vessel 2 dipped in the sample solution A, of which the bottom wall 3 is formed of the inventive polymeric membrane, contains an aqueous reference solution B of the objective cations in a known concentration of, usually, $10^{-6}$N to 1N. A first electrode 4 dipped in the reference solution B and a second electrode 5 dipped directly in the sample solution A are connected to the terminals of a potentiometer 6. In this assembly with the membrane electrode 3 contacting the sample solution A and reference solution B on both surfaces, a potential difference is produced at the interfaces of the membrane and the solutions and inside the membrane and can be determined on the potentiometer 6 connected to the electrodes 4 and 5, from which the activity of the cations in the sample solution A is calculated.

In the following, the electrode membrane of the invention is described in more detail by way of examples.

EXAMPLE 1

A uniform solution of polymeric composition was prepared by dissolving 0.10 g of a polyvinyl chloride resin, 0.25 g of 2-nitrophenyl octyl ether, 0.005 g of 2,9-dimethyl-1,10-phenanthroline and 0.003 g of potassium tetrakis(4-chlorophenyl) borate in 4 ml of tetrahydrofuran and a polymeric film having a thickness of about 0.2 mm and a diameter of 4.2 cm was prepared by casting of the solution and evaporation of the solvent.

An assembly for the determination of the potential difference as illustrated in the accompanying drawing was constructed, in which the electrode membrane had a diameter of 5 mm as taken from the above prepared polymeric film. The reference solution was an aqueous solution of lithium chloride in a concentration of 0.01N. Several aqueous solutions were prepared to serve as a simulated sample solution including aqueous solutions of potassium chloride, sodium chloride and lithium chloride each in a concentration of 0.01N, 0.1N or 1.0N and aqueous solutions of calcium chloride and magnesium chloride each in a concentration of 0.00002N, 0.0002N, 0.002N, 0.02N or 0.2N. The test was performed at 25° C. The calibration curve in each measurement exhibited sub-Nernstian response.

Calculation was made for the ion-selectivity of the electrode membrane log $K_{Li,j}{}^{pot}$ against the changes in the activity of the cations in the sample solutions to give the results of: zero for lithium ions; $-2.5$ for sodium ions; $-3.0$ for potassium ions; $-2.9$ for magnesium ions; and $-2.9$ for calcium ions. These results indicate that the electrode membrane of the invention gives a selective response of electromotive force for Li+ ions relative to the cations of the other alkali and alkaline earth metals against the changes in the activity thereof under the above specified experimental conditions.

EXAMPLE 2

The experimental procedure was substantially the same as in Example 1 excepting the replacement of the 2,9-dimethyl-1,10-phenanthroline with the same amount of 2,9-dimethyl-4,7-diphenyl-1,10-phenanthroline. The values of the ion-selectivity of the membrane log $K_{Li,j}{}^{pot}$ against the changes in the activity of the cations in the sample solutions calculated from the results of the potentiometric measurement were: zero for lithium ions; $-3.0$ for sodium ions; $-3.3$ for potassium ions; $-2.0$ for magnesium ions; and $-3.0$ for calcium ions. These results indicate that the electrode membrane of the invention gives a selective response of electromotive force for Li+ ions relative to the cations of the other alkali and alkaline earth metals against the changes in the activity thereof under the experimental conditions.

EXAMPLE 3

The experimental procedure was substantially the same as in Example 1 excepting replacement of the polyvinyl chloride resin with a poly(1,2-butadiene). The values of log $K_{Li,j}{}^{pot}$ obtained for various cations were: zero for lithium ions; $-2.0$ for sodium ions; $-2.2$ for potassium ions; $-1.5$ for magnesium ions; and $-1.8$ for calcium ions.

EXAMPLE 4

The experimental procedure was substantially the same as in Example 1 excepting omission of the potassium tetrakis(4-chlorophenyl) borate in the preparation of the membrane. The values of log $K_{Li,j}{}^{pot}$ obtained for various cations were: zero for lithium ions; $-1.2$ for sodium ions; $-1.6$ for potassium ions; $-0.9$ for magnesium ions; and $-1.6$ for calcium ions.

What is claimed is:

1. An electrode membrane having selectivity for lithium ions which is shaped from a polymeric composition comprising, in admixture;
   (a) a polymeric material;
   (b) a plasticizer; and
   (c) an aromatic compound having a structure of 1,10-phenanthroline represented by the general formula

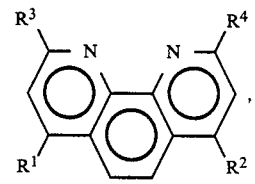

in which $R^1$ and $R^2$ are each an atom or group selected from the class consisting of a hydrogen atom, alkyl groups, aryl groups and aralkyl groups and $R^3$ and $R^4$ are each a group selected from the class consisting of alkyl groups, aryl groups and aralkyl groups.

2. The electrode membrane as claimed in claim 1 wherein the aromatic compound as the component (c) is selected from the group consisting of 2,9-dimethyl-1,10-phenanthroline, 2,9-dimethyl-4,7-diphenyl-1,10-phenanthroline, 2,9-dibutyl-1,10-phenanthroline, 2,9-dibutyl-4,7-diphenyl-1,10-phenanthroline, 2,9-dioctyl-1,10-phenanthroline, 2,9-dibenzyl-1,10-phenanthroline and 2,9-diphenyl-1,10-phenanthroline.

3. The electrode membrane as claimed in claim 1 wherein the polymeric composition comprises 100 parts by weight of the polymeric material as the component (a), from 10 to 300 parts by weight of the plasticizer as the component (b) and from 0.1 to 15 parts by weight of the aromatic compound as the component (c).

4. The electrode membrane as claimed in claim 1 wherein the polymeric composition further comprises an alkali metal salt of a hydrophobic anion.

5. The electrode membrane as claimed in claim 4 wherein the amount of the alkali metal salt of a hydrophobic anion is from 0.5 to 15 parts by weight per 100 parts by weight of the polymeric material as the component (a).

6. The electrode membrane as claimed in claim 1 wherein the polymeric material as the component (a) is a polyvinyl chloride resin of a poly(1,2-butadiene).

7. The electrode membrane as claimed in claim 1 wherein the plasticizer is selected from the group consisting of dialkyl aryl phosphonates, trialkyl phosphates, trialkyl phosphites, dialkyl sebacates, dialkyl adipates, dialkyl phthalates, nitrophenyl alkyl ethers and 2-nitrophenyl aryl ethers.

8. The electrode membrane as claimed in claim 6 wherein the plasticizer as the component (b) is 2-nitrophenyl octyl ether.

9. The electrode membrane as claimed in claim 1 which has a thickness in the range from 0.02 mm to 1 mm.

* * * * *

UNITED STATES PATENT AND TRADEMARK OFFICE
CERTIFICATE OF CORRECTION

PATENT NO. : 4,861,455
DATED : August 29, 1989
INVENTOR(S) : Sugihara, Hideki; Hiratani, Kazuhisa and Okada, Tatsuhiro It is certified that error appears in the above—identified patent and that said Letters Patent is hereby corrected as shown below:

On the title page:
Item [73] change:"Director General of Agency of Industrial Science and Technology"to read --Japan as represented by Director General of Agency of Industrial Science and Technology Signed and Sealed this Sixteenth Day of October, 1990

*Attest:*

HARRY F. MANBECK, JR.

*Attesting Officer*    *Commissioner of Patents and Trademarks*